United States Patent [19]
Eilingsfeld et al.

[11] 3,978,144
[45] Aug. 31, 1976

[54] MANUFACTURE OF O-BENZYLTOLUENES

[75] Inventors: Heinz Eilingsfeld, Frankenthal; Manfred Patsch, Ludwigshafen, both of Germany

[73] Assignee: BASF Aktiengesellschaft, Ludwigshafen (Rhine), Germany

[22] Filed: July 12, 1974

[21] Appl. No.: 488,003

[30] Foreign Application Priority Data
July 17, 1973 Germany............................ 2336289

[52] U.S. Cl. .......................... 260/649 R; 260/668 C
[51] Int. Cl.² .................... C07C 17/00; C07C 25/18
[58] Field of Search ...................... 260/649 R, 668 C

[56] References Cited
UNITED STATES PATENTS

| | | | |
|---|---|---|---|
| 2,600,691 | 6/1952 | Ross et al........................ | 260/649 R |
| 2,953,609 | 9/1960 | Wadsworth et al............. | 260/649 R |
| 3,006,972 | 10/1961 | Fields et al...................... | 260/649 R |

OTHER PUBLICATIONS

Holmberg, Chemical Abstracts, 45 559g, (1951).

*Primary Examiner*—D. Horwitz
*Attorney, Agent, or Firm*—Johnston, Keil, Thompson & Shurtleff

[57] ABSTRACT

The manufacture of o-benzyltoluenes by reaction of o-xylyl halides with benzenes in the presence of boron trifluoride or its derivatives, and new o-benzyltoluenes. The new and known o-benzyltoluenes I manufactured by the process of the invention are starting materials for the manufacture of anthracene and anthraquinone and their derivatives.

9 Claims, No Drawings

MANUFACTURE OF O-BENZYLTOLUENES

This invention is concerned with a process for the manufacture of -o-benzyltoluenes by reaction of o-xylyl halides with benzenes in the presence of boron trifluoride or its derivatives, and with new o-benzyltoluenes.

O-benzyltoluene results, alongside other products, when toluene is heated with benzyl chloride in the presence of zinc dust (Chemische Berichte, volume 6, pages 906 et seq (1873)) or of beryllium chloride (Chemische Berichte, volume 72, pages 1,414 et seq (1939)). Treatment of a mixture of o-xylyl chloride and benzene with zinc dust also gives o-benzyltoluene, in poor yield (Chemische Berichte, volume 7, pages 1,544 et seq (1874)). All these processes are unsuitable for industrial exploitation since they either give poor yields or mixtures which are difficult to separate. The hydrogenation of o-benzoylbenzoic acid ethyl ester in the presence of copper chromite at 250°C also gives o-benzyltoluene (J. Amer. Chem. Soc., volume 55 (1933), pages 1,699 et seq). The manufacture of the catalyst, and, in particular, the multi-step manufacture of the starting material are involved and uneconomical, so that this process is also unsatisfactory in that it does not provide simple, economical and trouble-free operation when used on a commercial scale.

It is an object of the present invention to provide a new process for manufacturing o-benzyltoluenes more simply and more economically, and in good yield and good purity.

A further object of the present invention is the new o-benzyltoluenes themselves.

We have found that o-benzyltoluenes of the formula

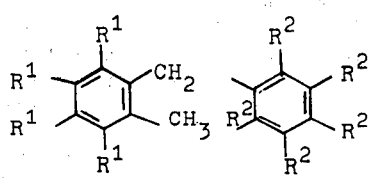

I in which the individual radicals $R^1$ are identical or different and each is hydrogen or halogen and the individual radicals $R^2$ are identical or different and each is hydrogen, halogen or an aliphatic or aromatic radical, are obtained by reaction of o-xylyl halides with aromatic compounds in an advantageous process wherein o-xylyl halides of the formula

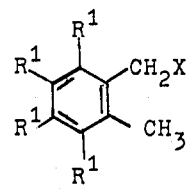

II wherein $R^1$ has the above meaning and X is halogen, are reacted with benzenes of the formula

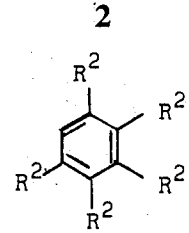

III wherein $R^2$ has the above meanings, in the presence of boron trifluoride or its derivatives and in the presence of an oxygen-containing acid which forms an adduct with the above boron compounds.

Where o-xylyl chloride and benzene are used, the reaction can be represented by the following equation:

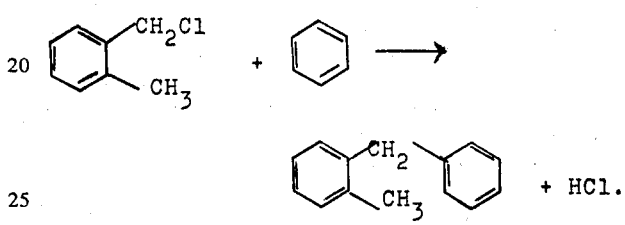

In comparison to the conventional processes, the process of the invention gives o-benzyltoluenes more simply and more economically, and in good yield and high purity. Compared to the conventional processes which use aralkyl chlorides, yield and purity of the end product are better and the isolation of the end product from the reaction mixture is much simpler and more reliable. Compared to the state of the art, the process according to the invention is simpler, less prone to breakdown and therefore suitable for commercial operation. The starting materials are readily obtainable and do not have to be manufactured by involved or multi-step syntheses. All these advantageous aspects are surprising in the light of the art, since it would have been expected, in Friedel-Crafts syntheses, that alkylated aromatics would be aralkylated much more readily than, for example, benzene, and that therefore o-xylyl halides would preferentially react with themselves and would only react to a minor degree with benzene.

The starting material III can be reacted with the starting material II in the stoichiometric ratio or using an excess of the former, preferably using a ratio of 1 to 20 moles of starting material III per mole of starting material II. Preferred starting materials II and III and, accordingly, preferred end products I are those in the formulae of which the individual radicals $R^1$ and $R^2$ are identical or different and are each hydrogen or chlorine or bromine, in addition the radicals $R^2$ can also be alkyl of 1 to 6 carbon atoms or phenyl, and X is bromine or, preferably, chlorine. The abovementioned radicals can furthermore be substituted by groups and/or atoms which are inert under the reaction conditions, for example alkyl of 1 to 4 carbon atoms.

Examples of suitable starting materials II are o-xylyl chloride, 3-chloro-2-chloromethyl-toluene, 4-chloro-2-chloromethyl-toluene, 5-chloro-2-chloromethyl-toluene, 6-chloro-2-chloromethyl-toluene, 6-bromo-2-chloromethyl-toluene, 4-bromo-2-chloromethyl-toluene, 3-bromo-2-chloromethyl-toluene, 5-bromo-2-chloromethyl-toluene and analogous bromomethyl compounds.

Examples of suitable starting materials II are: Benzene, toluene, o-xylene, m-xylene, p-xylene, diphenyl, 1,4-diphenylbenzene, 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, pentamethylbenzene, chlorobenzene, 1,4-dichlorobenzene, bromobenzene, o-chlorotoluene, m-chlorotoluene, p-chlorotoluene, p-bromo-ethyl-benzene, tert.-butylbenzene and 4,4'-dichlorodiphenyl.

In general, the reaction is carried out batchwise or continuously at temperatures from 40° to 160°C and preferably from 60° to 130°C, at atmospheric or superatmospheric pressure. Preferably, solvents which are inert under the reaction conditions are used, for example water, aromatic hydrocarbons such as nitrobenzene and trichlorobenzene, chlorohydrocarbons such as methylene chloride, ethylene chloride, carbon tetrachloride and chloroform, carbon disulfide, aliphatic hydrocarbons such as ligroin or petroleum ether, or corresponding mixtures. Amounts of 10 to 100% by weight of solvent, based on starting material II, can be used. The starting material itself can also serve as the solution medium.

The reaction is carried out in the presence of an acid which contains one or more oxygen atoms in the molecule or, where complex compounds are used as acids, in the structural formula. The acids can form adducts such as Lewis acids, or complex compounds, with boron trifluoride or its derivatives. Inorganic or organic acids or Lewis acids can be used as the acids. The definition of Lewis acids can be found in Houben-Weyl, Methoden der Organischen Chemie, volume 4/2, page 6. Instead of monobasic acids, equivalent amounts of polybasic acids can be employed. Examples of suitable acids are phosphoric acid; sulphonic acids, such as benzenesulfonic acid and p-toluenesulfonic acid; acids containing boron, which can also be Lewis acids, such as boric acid, boron trifluoride dihydrate, and adducts (complex compounds) of boron trifluoride with ethanol or phosphoric acid; and aliphatic carboxylic acids such as propionic acid, butyric acid, oxalic acid, formic acid, acetic acid and adipic acid. The acids can be used in the concentrated form, as mixtures with one another, and/or as mixtures with a solvent, in particular water. Acetic acid and especially phosphoric acid are preferred. The amounts used are from 1 to 100% by weight of acid, based on starting material II.

Boron trifluoride can be introduced into the reaction mixture as a gas but is preferably employed in the form of solutions, for example in water, phosphoric acid or acetic acid. Not only boron trifluoride but also its derivatives, such as Lewis acids, complex compounds and adducts can be used. Examples of suitable derivatives are its dihydrate and its adducts or complex compounds with ethanol or phosphoric acid or ethers, for example with diethyl ether. It is also possible to use materials which form such complex compounds under the reaction conditions, for example alkali metal phosphates and boron trifluoride in an acid reaction mixture. In the complex compound or adduct, the molar ratio of noron trifluoride and the complexing agent or agent which forms an adduct is in general 1 to 1 whilst in the case of water as the agent it is 1 to 2. In general, from 0.1 to 10, preferably from 0.5 to 5, moles of boron trifluoride, or boron trifluoride present in its derivative, are used per mole of starting material II.

In a preferred embodiment, adducts (complex compounds) of boron trifluoride or its derivatives, which form oxygen-containing acids under the reaction conditions are used simultaneously as both catalyst and acid. Examples of advantageous compounds are boron trifluoride dihydrate and boron trifluoride/ethanol complex compounds. Adducts (complex compounds) with phosphoric acid, in particular boron trifluoride/phosphoric acid, are particularly preferred for use in the process according to the invention.

The reaction can be carried out as follows: A mixture of the starting materials II and III, boron trifluoride or its derivative, the acid and the solvent, if any, is kept at the reaction temperature for from 2 to 15 hours, whilst being subjected to thorough mixing. The mixture is then cooled and the end product is isolated by conventional methods, for example by separating off the organic phase and distilling it.

The side-chain halogenation of haloxylenes to give the starting materials II, for example the side-chain chlorination of 3-chloro-o-xylene or 4-chloro-o-xylene, in each case produces two isomeric halo-o-xylyl halides, which in the examples chosen are 3-chloro-2-chloromethyl-toluene and 6-chloro-2-chloromethyl-toluene, and 4- and 5-chloro-2-chloromethyl-toluene, respectively; these, on reaction with benzenes III, in each case give two correspondingly isomeric benzyl-chloro-toluenes. The oxidation of the mixtures to the corresponding o-benzoylbenzoic acids and subsequent cyclization gives anthraquinones which have the same substitution, in the examples chosen 1-chloro-anthraquinone and 2-chloro-anthraquinone respectively. Whilst the end products I can be isolated from the said mixtures by suitable operations, for example fractional distillation or fractional crystallization, it will in general be preferred to react mixtures of such starting materials II and to use the resulting mixture of end products I directly for subsequent processes. For the same reason, it will in most cases be convenient to subject mixtures of 3-chloro-o-xylene and 4-chloro-o-xylene, such as are obtained, for example, on chlorinating o-xylene, to side-chain chlorination, react the resulting mixture of 4 isomeric starting materials II using the process according to the invention, and separate the resulting mixture of the 4 end products I only after cyclization to the chloro-anthracenes. The process according to the invention is this significant not only for the manufacture of individual end products, but also for the manufacture of the mixtures described, which are important starting materials for the synthesis of dyestuffs, particularly on an industrial scale.

The new and known o-benzyltoluenes I manufactured by the process of the invention are valuable starting materials for the manufacture of anthracene and anthraquinone, and their derivatives. Thus anthracene derivatives are obtained on passing the vapors of o-benzyltoluenes over lead oxide. Oxidation with nitric acid gives o-benzoylbenzoic acid and its derivatives. The uses are described in the publications cited above, and in Ullmanns Encyklopadie der technischen Chemie, volume 3, pages 660 et seq.

Advantageous new end products I in this context are o-benzyltoluenes of the formula

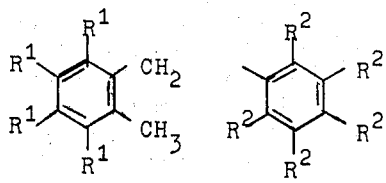 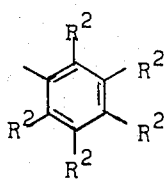

wherein the individual radicals R¹ are identical or different and each is hydrogen or halogen and the individual radicals R² are identical or different and each is an aromatic radical, and in addition the individual radicals R² can each be hydrogen or an aliphatic radical if at least one radical R¹ is halogen, or all radicals R¹ can be hydrogen if at least one radical R² is an aromatic radical and the remaining radicals R² are each hydrogen, halogen and/or an aliphatic radical or if, simultaneously, at least one radical R² is halogen, at least one radical R² is an aliphatic radical and the remaining radicals R² are each hydrogen, halogen and/or an aliphatic radical.

Preferred hitherto unknown end products I are o-benzyl-toluenes of the formula

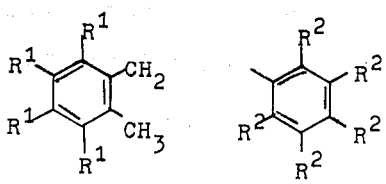 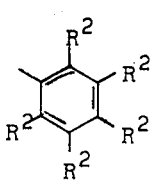

wherein the individual radicals R¹ are identical or different and each is hydrogen or chlorine or bromine, and the individual radicals R² are identical or different and each is phenyl, and in addition the individual radicals R² can each be hydrogen or alkyl or 1 to 6 carbon atoms if at least one radical R¹ is chlorine or bromine, or all radicals R¹ can be hydrogen if at least one radical R² is phenyl and the remaining radicals R² are each hydrogen, chlorine, bromine and/or alkyl of 1 to 6 carbon atoms or if, simultaneously, at least one radical R² is chlorine or bromine, at least one radical R² is alkyl of 1 to 6 carbon atoms and the remaining radicals R² are each hydrogen, chlorine, bromine and/or alkyl of 1 to 6 carbon atoms.

Particularly preferred new o-benzyltoluenes are those of the formula

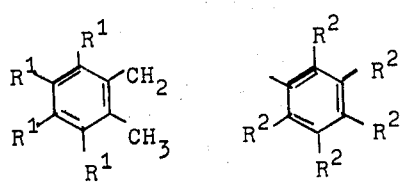

wherein the individual radicals R¹ are identical or different and each is hydrogen or chlorine but at least one radical R¹ is chlorine, and the individual radicals R² are each hydrogen. Further preferred new end products I are, in particular, these o-benzyltoluenes of the formula

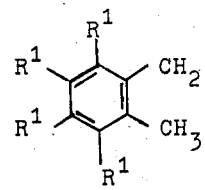

I

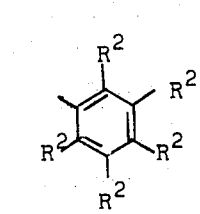

wherein the individual radicals R¹ are each hydrogen and the individual radicals R² are identical or different and at least one radical R² is phenyl or one radical R² is chlorine and a further radical R² is methyl and the remaining radicals R² are each hydrogen.

Examples of particularly preferred new end products I are 2-benzyl-3-chlorotoluene, 2-benzyl-6-chlorotoluene, 2-benzyl-4-chlorotoluene, 2-benzyl-5-chlorotoluene, 2,2'-dimethyl-5-chlorodiphenylmethane and 2-methyl-4'-phenyl-diphenylmethane.

The parts mentioned in the Examples are parts by weight.

EXAMPLE 1

A solution of 280 parts of o-xylyl chloride in 520 parts of benzene is added to a mixture of 520 parts of benzene and 200 parts of boron fluoride/phosphoric acid (containing 90 parts of boron trifluoride in 110 parts of phosphoric acid) at from 75° to 80°C in the course of one hour. The reaction mixture is stirred for a further three hours at 80°C and allowed to cool, the aqueous solution is separated off and the organic phase is distilled. Yield 322 parts (88.4% of theory) of o-benzyltoluene of boiling point from 145° to 149°C at 17 mm Hg.

EXAMPLE 2

The procedure of Example 1 is followed, using 100 parts of boron trifluoride dihydrate as the catalyst, in place of the adduct of boron trifluoride and phosphoric acid. 136 parts (70% of theory) of o-benzyltoluene of boiling point from 145° to 149°C at 17 mm Hg are obtained.

EXAMPLE 3

A mixture of 95 parts of 2-chloromethyl-6-chlorotoluene, 80 parts of 2-chloromethyl-3-chlorotoluene and 250 parts of benzene is added to a mixture of 250 parts of benzene and 180 parts of boron fluoride/phosphoric acid (containing 80 parts of boron trifluoride in 100 parts of phosphoric acid) at from 75° to 80°C in the course of one hour. After a further 6 hours at 80°C, the organic phase is separated off and fractionated. 148 parts (68.4% of theory) of a mixture of 78 parts of 2-benzyl-6-chlorotoluene and 70 parts of 2-benzyl-3-chlorotoluene distil at from 175° to 177°C at 17 mm Hg.

EXAMPLE 4

A mixture of 85 parts of 2-chloromethyl-5-chiorotoluene, 85 parts of 2-chloromethyl-4-chlorotoluene and 250 parts of benzene and 180 parts of boron fluoride/phosphoric acid (containing 80 parts of boron trifluoride in 100 parts of phosphoric acid) at from 75° to 80°C in the course of one hour. After a further 6 hours at 80°C, the organic phase is separated off and 150 parts (69.3% of theory) of a mixture of 75 parts of 2-benzyl-4-chlorotoluene and 75 parts of 2-benzyl-5-chlorotoluene are obtained by fractional distillation at from 175° to 178°C and 16 mm Hg.

EXAMPLE 5

A mixture of 40 parts of 3-chloro-o-xylyl chloride, 45 parts of 4-chloro-o-xylyl chloride, 45 parts of 5-chloro-o-xylyl chloride and 45 parts of 6-chloro-o-xylyl chloride in 250 parts of benzene is added to a mixture of 250 parts of benzene and 260 parts of boron fluoride/phosphoric acid (containing 110 parts of boron fluoride in 150 parts of phosphoric acid) at from 75° to 80°C in the course of one hour. After a further 8 hours at 80°C, the organic phase is separated off and subjected to fractional distillation. 165 parts (76.3% of theory) of a mixture of isomeric monochloro-o-benzyltoluenes of boiling point from 116° to 118°C at 0.3 mm Hg are obtained.

EXAMPLE 6

A mixture of 28 parts of o-xylyl chloride and 40 parts of p-chlorotoluene is added to a mixture of 40 parts of p-chlorotoluene and 29 parts of boron fluoride/phosphoric acid (containing 9 parts of boron trifluoride in 20 parts of phosphoric acid) at from 85° to 90°C in the course of one hour. After a further 8 hours at from 90° to 100°C, the organic phase is separated off and subjected to fractional distillation. 22 parts (47.8% of theory) of 2,2'-dimethyl-5-chlorodiphenylmethane of boiling point from 126° to 128°C at 0.2 mm Hg are isolated.

EXAMPLE 7

A solution of 28 parts of o-xylyl chloride in 50 parts of o-xylene is added to a mixture of 50 parts of o-xylene and 14.5 parts of boron fluoride/phosphoric acid) at from 95° to 100°C in the course of 2 hours. The reaction mixture is stirred for a further 4 hours at from 95° to 100°C, the organic phase is separated off, and 35 parts (83.4% of theory) of 2,3',4'-trimethyldiphenylmethane (boiling point from 110° to 112°C at 0.05 mm Hg) are isolated by fractional distillation.

EXAMPLE 8

The reaction is carried out analogously to Example 7 with p-xylene instead of o-xylene. 32 parts (76.2% of theory) of 2,2',5'-trimethyldiphenylmethane of boiling point from 104° to 106°C at 0.2 mm Hg are obtained.

EXAMPLE 9

A solution of 28.1 parts of o-xylyl chloride in 50 parts of ligroin is added to a mixture of 61.4 parts of diphenyl, 150 parts of ligroin and 110 parts of boron fluoride/phosphoric acid (containing 30 parts of boron fluoride in 80 parts of phosphoric acid) at from 75° to 80°C in the course of 2 hours. After a further 7 hours at from 75° to 80°C, the organic phase is separated off and 31.5 parts (61% of theory) of 2-methyl-4'-phenyldiphenylmethane, of boiling point from 190° to 193°C at 0.3 mm Hg, are isolated by fractional distillation.

EXAMPLE 10

A solution of 92.5 parts of o-xylyl bromide in 120 parts of benzene is added to a mixture of 120 parts of benzene and 70 parts of boron fluoride/phosphoric acid (containing 20 parts of boron trifluoride in 50 parts of phosphoric acid) at from 60° to 70°C in the course of 3 hours. After a further 5 hours at from 70° to 80°C the organic phase is separated off and 37.3 parts (41% of theory) of o-benzyltoluene of boiling point from 94° to 97°C (0.3 mm Hg) are isolated by fractional distillation.

EXAMPLE 11

A solution of 28.1 parts of o-xylyl chloride in 70 parts of chlorobenzene is added to a mixture of 70 parts of chlorobenzene and 29 parts of boron fluoride/phosphoric acid (containing 9 parts of boron fluoride in 20 parts of phosphoric acid) in the course of 2 hours at from 95° to 100°C. After a further 7 hours at from 95° to 100°C, the organic phase is separated off and 20 parts (46.2% of theory) of 2-methyl-4'-chlorodiphenylmethane of boiling point from 118° to 120°C (0.1 mm Hg) are isolated by fractional distillation.

We claim:
1. In a process for the manufacture of o-benzyltoluenes of the formula

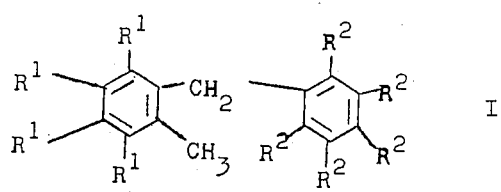

wherein $R^1$ is hydrogen, chlorine or bromine, $R^2$ is hydrogen, chlorine, bromine, alkyl of 1 to 6 carbon atoms, phenyl or phenyl substituted by alkyl of 1 to 4 carbon atoms, by reaction of an o-xylyl halide with an aromatic compound, the improvement which comprises:
reacting an o-xylyl halide of the formula

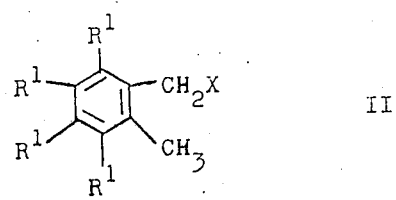

wherein R¹ has the above meanings and X is bromine or chlorine with a benzene of the formula

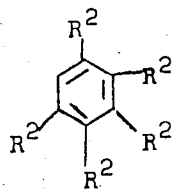   III wherein R² has the above meanings, in the presence of boron trifluoride or derivatives thereof in the form of its dihydrate or its adducts or complex compounds with ethanol, phosphoric acid or diethyl ether and in the presence of an oxygen-containing acid which forms an adduct with the above boron compounds the said acid being selected from the group consisting of phosphoric acids, sulphonic acids, acids containing boron, propionic acid, butyric acid, oxalic acid, formic acid, acetic acid and adipic acid.

2. A process as claimed in claim 1, wherein the reaction is carried out with a ratio of 2 to 20 moles of starting material III per mole of starting material II.

3. A process as claimed in claim 1, wherein the reaction is carried out at from 40° to 60°C.

4. A process as claimed in claim 1, wherein the reaction is carried out at from 60° to 130°C.

5. A process as claimed in claim 1, wherein the reaction is carried out in the presence of 10 to 100% by weight, based on starting material II, of solvents which are inert under the reaction conditions.

6. A process as claimed in claim 1, wherein the reaction is carried out with from 1 to 100% by weight of acid, based on starting material II.

7. A process as claimed in claim 1, wherein the reaction is carried out with from 0.1 to 10 moles of boron trifluoride, or boron trifluoride contained in the derivative, per mole of starting material II.

8. A process as claimed in claim 1, wherein the reaction is carried out with from 0.5 to 5 moles of boron trifluoride, or boron trifluoride contained in the derivative, per mole of starting material II.

9. A process as claimed in claim 1, wherein the reaction is carried out with boron trifluoride dihydrate, boron trifluorideethanol complex compounds of boron fluoride-phosphoric acid.

* * * * *